United States Patent [19]

Singh et al.

[11] Patent Number: 4,839,465

[45] Date of Patent: Jun. 13, 1989

[54] DI-(D-TRYPTOPHYL AND/OR TETRAHYDROPYRIDOINDOLYLCARBONYL)-CONTAINING PEPTIDE AMIDES AND PROCESS FOR PREPARATION THEREOF

[75] Inventors: Jasbir Singh; Barry A. Morgan, both of Albany, N.Y.

[73] Assignee: Sterling Drug Inc., New York, N.Y.

[21] Appl. No.: 5,495

[22] Filed: Jan. 20, 1987

[51] Int. Cl.$^4$ .................................................. C07K 7/06
[52] U.S. Cl. .................................... 530/330; 530/329; 530/331
[58] Field of Search ............... 530/327, 330, 328, 329, 530/327, 331

[56] References Cited

U.S. PATENT DOCUMENTS 4,472,305 9/1984 Hansen et al. ................ 260/112.5 R
4,481,139 11/1984 Folkers et al. ....................... 530/327

FOREIGN PATENT DOCUMENTS 3205991 9/1983 Fed. Rep. of Germany ...... 530/327

OTHER PUBLICATIONS

Yabe et al., Chem. Pharm. Bull., vol. 25, pp. 2731–2734, 1977.
Yabe et al. Chem. Pharm. Bull., vol. 26, pp. 993–997, 1978.

Primary Examiner—Delbert R. Phillips
Assistant Examiner—T. D. Wissendorf
Attorney, Agent, or Firm—Theodore C. Miller; Paul E. Dupont

[57] ABSTRACT

Di(D-tryptophyl and/or tetrahydropyridoindolylcarbonyl)-containing peptide amides useful as Substance P agonists and/or antagonists and as antihypertensives and/or analgesics and a process for preparing them are disclosed.

18 Claims, No Drawings

DI-(D-TRYPTOPHYL AND/OR TETRAHYDROPYRIDOINDOLYLCARBONYL)-CONTAINING PEPTIDE AMIDES AND PROCESS FOR PREPARATION THEREOF

BACKGROUND OF THE INVENTION

1. Field of the Invention

The invention relates to di-(D-tryptophyl and/or tetrahydropyridoinolylcarbonyl)-containing peptide amides which are useful as Substance P agonists and/or antagonists and are therefore useful as antihypertensives and/or analgesics.

2. Information Disclosure Statement

Substance P (SP) is an endogenous undecapeptide amide and a putative neurotransmitter of mammalian central nervous systems (Sandberg et al., J. Med. Chem., vol. 25, no. 9, pp. 1009–1015, 1982) having the following structural formula, wherein the amino acid units are numbered from 1 through 11 beginning with the N-terminal amino acid:

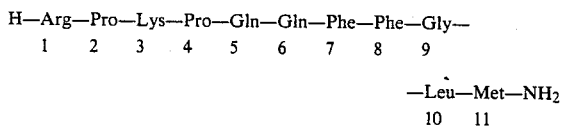

The hexapeptide amide having the structural formula

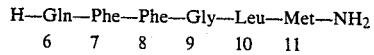

is referred to as $SP_{6-11}$.

Hansen et al. U.S. Pat. No. 4,472,305 issued Sept. 18, 1984 describes Substance P agonist and/or antagonist hexapeptide amides related to $SP_{6-11}$ including the product of example 17 having in its free base form the structural formula

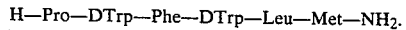

Yabe et al. (Chem. Pharm. Bull., vol. 25, pp. 2731–2734, 1977) describes the peptide having the structural formula

having gastric juice stimulating activity, which is otherwise described therein as Tca-tetragastrin. Tca (H—Tca—OH) is defined as 1,2,3,4-tetrahydro-β-carboline-3-carboxylic acid having the L-configuration.

Yabe et al. (Chem. Pharm. Bull., vol. 26, pp. 993–997, 1978) describes $Tca^8$-somastatin (somastatin is a cyclic tetradecapeptide), which showed inhibition of thyrotropin releasing hormone (TRH)-induced thyrotropin stimulating hormone (TSH) release in the rat.

SUMMARY OF THE INVENTION

In a first composition of matter aspect the invention is the peptide amide having the structural formula

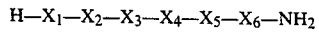    Formula I wherein
$X_1$ is a direct linkage or Pro;
$X_2$ is trp, Tpi or tpi;
$X_3$ is Phe, Bpa or bpa;
$X_4$ is trp or tpi;
$X_5$ is Leu or a direct linkage; and
$X_6$ is Met, Phe or a direct linkage;
except that $X_1$ cannot be Pro when $X_6$ is Met; or a pharmaceutically acceptable acid addition salt and/or solvate thereof.

In a second composition of matter aspect the invention is the peptide amide of Formula I wherein $X_1$, $X_2$, $X_3$, $X_4$, $X_5$ and $X_6$ have the definitions set forth above, except that at least one of $X_2$ and $X_4$ is other than trp, or a pharmaceutically acceptable acid addition salt and/or solvate thereof.

In a third composition of matter aspect the invention is the peptide amide of Formula I wherein $X_1$, $X_2$, $X_3$, $X_4$, $X_5$ and $X_6$ have the definitions set forth above, except that when $X_2$ is trp $X_4$ is also trp and that $X_1$ cannot be Pro when $X_6$ is Met, or a pharmaceutically acceptable acid addition salt and/or solvate thereof.

The peptide amides of the three composition of matter aspects of the invention are useful as Substance P agonists and/or antagonists and are therefore useful as antihypertensives and/or analgesics.

In a process aspect the invention is the process of preparing a peptide amide in accordance with one of the three composition of matter aspects of the invention which comprises condensing the corresponding amino acid and/or peptide moieties by an $X_1+X_{2-6}$, $X_{1-2}+X_{3-6}$, $X_{1-3}+X_{4-6}$, $X_{1-4}+X_{5-6}$ or $X_{1-5}+X_6$ hexapeptide forming method when $X_1$, $X_5$ and $X_6$ are other than a direct linkage, an $X_2+X_{3-6}$, $X_{2-3}+X_{4-6}$, $X_{2-4}+X_{5-6}$ or $X_{2-5}+X_6$ pentapeptide forming method when $X_1$ is a direct linkage and $X_5$ and $X_6$ are other than a direct linkage, an $X_2+X_{3-5}$, $X_{2-3}+X_{4-5}$ or $X_{2-4}+X_5$ tetrapeptide forming method when $X_1$ and $X_6$ are direct linkages and $X_5$ is other than a direct linkage, or an $X_2+X_{3-4}$ or $X_{2-3}+X_4$ tripeptide forming method when $X_1$, $X_5$ and $X_6$ are direct linkages, concomitantly protecting and deprotecting the N-terminal α-amino group and the C-terminal carboxyl group as required.

In the definitions of $X_1$, $X_2$, $X_3$, $X_4$, $X_5$ and $X_6$ above and in the examples below the symbols for the amino acid moieties, which do not include the N-terminal and C-terminal groups, have the following meanings:
Pro: L-prolyl
trp: D-tryptophyl
Tpi: S-(2,3,4,9-tetrahydro-1H-pyrido[3,4-b]indol-3-yl)-carbonyl, or L-(1,2,3,4-tetrahydro-β-carboline-3-carbonyl) having the structural formula

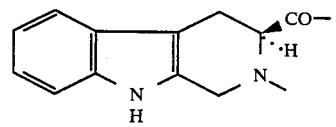

wherein the configuration at the 3-position is that if an L-amino acid
tpi: R-(2,3,4,9-tetrahydro-1H-pyrido[3,4-b]indol-3-yl)-carbonyl or D-(1,2,3,4-tetrahydro-β-carboline-3-carbonyl) having the structural formula

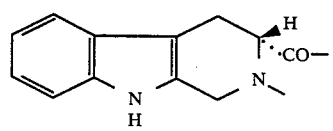

wherein the configuration at the 3-position is that of a D-amino acid
Phe: L-phenylalanyl
Bpa: L-β-(2,3 or 4-pyridyl)alanyl
bpa: D-β-(2,3 or 4-pyridyl)alanyl
Leu: L-leucyl
Met: L-methionyl

DETAILED DESCRIPTION OF THE INVENTION INCLUSIVE OF THE PREFERRED EMBODIMENTS

Preparation of the Compounds

The protection, activation, condensation and deprotection steps required to prepare the compounds of the three composition of matter aspects of the invention are carried out using the methods of peptide synthesis generally described by Houben Weyl "Methoden der Organischen Chemie" (vol. 16, parts I and II, "Synthese von Peptiden", Thieme, 1974) and Gross and Meienhofer "The Peptides" (vol. 1, "Major Methods of Peptide Bond Formation", Academic Press, 1979).

The suitably carboxyl-activated derivatives of the amino acid and peptide intermediates can be formed and used with or without being isolated and include the acyl halides and pseudohalides, especially the acyl azides; the anhydrides, especially the mixed anhydrides and most especially the mixed anhydride with diphenylphosphinyl chloride or isobutyl chloroformate; derivatives formed by addition reactions, especially using dicyclohexylcarbodiimide; displaceable acyl derivatives of heterocyclic nitrogen; ring-openable activated heterocyclic systems; acylphosphonium derivatives; and activated esters, especially 1-hydroxybenzotriazole (HOBt), N-hydroxysuccinimide (HOSu) and pentafluorophenyl (PFP) esters. In carrying out solid phase (Merrifield) peptide synthesis the preferred carboxyl-activated amino acid derivative is the symmetrical anhydride.

It is necessary that the N-terminal α-amino group be protected during the peptide forming steps. The preferred α-amino protecting groups are benzyloxycarbonyl (Z), which can be removed by catalytic hydrogenation using palladium as catalyst or by hydrogen bromide in acetic acid, and t-butyloxycarbonyl (Boc), which can be removed by acidic cleavage, for example, with hydrogen chloride in a suitable solvent or trifluoroacetic acid with or without a solvent or liquid hydrogen fluoride and anisole. A protecting group which can be removed in the presence of benzyloxycarbonyl or t-butyloxycarbonyl under basic conditions, for example piperidine in dimethylformamide, is 9-fluorenylmethoxycarbonyl (Fmoc).

The C-terminal carboxyl group must also be protected during the peptide forming steps. That of the compounds of the three composition of matter aspects of the invention is protected as the amide, which is a required structural feature thereof and is therefore not removed, except in solid phase peptide synthesis, wherein the C-terminal carboxyl group is protected as a resin-bonded benzylic ester (Bzl-resin) and converted into the amide by ammonolysis in the penultimate step. The C-terminal carboxyl groups of the intermediate amino acids and peptides can be protected as the carboxylate salt, and t-butyl (tBu) ester, which can be removed by acidic cleavage, for example, with hydrogen chloride or trifluoroacetic acid in a suitable solvent, the benzyl (Bzl) ester, which can be removed by catalytic hydrogenation using palladium as catalyst or the methyl ester, which can be removed by alkaline hydrolysis.

The intermediate amino acids and peptides and the protected derivatives thereof necessary to prepare the compounds of the three composition of matter aspects of the invention are known classes of compounds and are commercially available or can be made by methods specifically or generally described in the chemical literature.

The acid addition salts of the compounds of the three composition of matter aspects of the invention are prepared by conventional methods from any of the pharmaceutically acceptable organic and inorganic acids. Of the inorganic acids hydrochloric acid and phosphoric acid are particularly preferred. Of the organic acids acetic acid is particularly preferred.

The compounds of the three composition of matter aspects of the invention and the acid addition salts thereof are hydrophilic and may form solvates with water or hydrophilic organic solvents or mixtures thereof. If the resulting products are crystalline, they are purified by recrystallization. If they are non-crystalline, which is generally so, they are purified by high pressure liquid chromatography or column chromatography and/or isolated by lyophilization.

In the preparations described below structures of products are inferred from known structures of starting materials and expected courses of preparative reactions. Structural confirmation and estimation of purity of starting materials and products are measured by melting temperature range (m.r.), optical rotation ($[\alpha]_D^{25}$), elemental analysis, infrared (IR) spectral analysis, ultraviolet (UV) spectral analysis, mass spectral (MS) analysis, nuclear magnetic resonance (NMR) spectral analysis, gas chromatography (GC), column chromatography, high pressure liquid chromatography (HPLC), medium pressure liquid chromatography (MPLC), thin layer chromatography (TLC) and/or amino acid analysis.

EXAMPLE 1

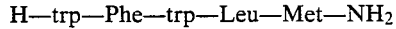
H—trp—Phe—trp—Leu—Met—NH$_2$

Condensation of Boc—trp—OH (15.2 g.) and H—Phe—OBzl p-toluenesulfonate salt (21.35 g.) by the mixed anhydride method using isobutyl chloroformate (6.96 g.) and N-methylmorpholine (two 5.05 g. portions) in tetrahydrofuran (400 ml.) and dimethylformamide (100 ml.) for two hours at −20° C. and then for one hour at room temperature gave Boc—trp—Phe—OBzl as a white solid (26.11 g., 96.5% yield).

Debenzylation of Boc—trp—Phe—OBzl (10.245 g.) by hydrogenation in a Parr shaker with palladium-on-carbon (10%, 1.0 g.) in ethanol (280 ml.) for two hours at room temperature gave Boc—trp—Phe—OH as a white solid (7.92 g., 92.7% yield, m.r. 208°–209° C.).

Condensation of Boc—trp—Phe—OH (2.22 g.) and H—trp—Leu—Met—NH$_2$ (example 17 of above-cited U.S. Pat. No. 4,472,305, 2.20 g.) using dicyclohexylcarbodiimide (1.05 g.) and N-hydroxysuccinimide (0.58 g.) in tetrahydrofuran (70 ml.) and dimethylformamide (10 ml.) at ice temperature for two hours and than at room temperature overnight gave Boc—trp—Phe—trp—Leu—Met—NH$_2$ (2.59 g., 60% yield).

De-t-butyloxycarbonylation of Boc—trp—Phe—trp—Leu—Met—NH$_2$ (2.58 g.) using trifluoroacetic acid (25 ml.) in dimethyl sulfide (25 ml.) and ethanedithiol (2.5 ml.) for fifteen minutes at ice temperature and then two hours at room temperature followed by treatment with sodium bicarbonate gave H—trp—Phe—trp—Leu—Met—NH₂ as the crystalline white solid free base (1.85 g., 82% yield, m.r. 166°-168° C.).

EXAMPLE 2

H—Pro—trp—Phe—trp—Leu—Phe—NH₂

Boc—Pro—trp—Phe—trp—Leu—Phe—OBzl-resin was prepared in 96% yield by solid phase peptide synthesis by the symmetrical anhydride method using a commercial (Vega 250C) synthesizer and starting with Boc—Phe—OBzl-resin (6.0 g., 0.68 mmol. of Phe/g. of resin), which was prepared from the cesium salt of Boc—Phe—OH (5.56 g.) and chloromethylated styrene-divinylbenzene (1%) copolymer (Bio-Beads X-X-2, 200-400 mesh, Bio-Rad Laboratories, 30 g.) in dimethylformamide. The N-terminal protecting group throughout the synthesis was t-butyloxycarbonyl. The anhydride-forming reagent was dicyclohexylcarbodiimide. The solvent for both anhydride formation and coupling was dichloromethanedimethylformamide.

Boc—Pro—trp—Phe—trp—Leu—Phe—OBz-resin (1.8 g.), dimethylformamide (40 ml.) and liquid ammonia (50 ml.) were combined in a stainless steel high pressure reaction flask with cooling in an ice-ethanol bath. Some of the mixture was lost by oozing. The flask was allowed to warm to room temperature and shaken. The reaction mixture was filtered and the resin was washed with dimethylformamide. The filtrate was concentrated under vacuum, then again after addition of methanol, and the residue was dried under high vacuum (320 mg.) and purified by reverse phase high pressure liquid chromatography on octadecylsilated silica gel using methanol-water (78:22) as eluant, affording Boc—Pro—trp—Phe—trp—Leu—Phe—NH₂ as a white solid (162 mg., 13% yield).

De-t-butyloxycarbonylation of Boc—Pro—trp—Phe—trp—Leu—Phe—NH₂ (160 mg.) using trifluoroacetic acid-water (60:40, 25 ml.) at room temperature and conversion of the product into the phosphate salt by ion exchange chromatography followed by lyophilization from water-t-butyl alcohol (80:20) gave H—Pro—trp—Phe—trp—Leu—Phe—NH₂ as the amorphous white solid phosphate salt (1:1) (180 mg.; theory, 160 mg.).

EXAMPLE 3

H—Pro—trp—Phe—trp—Leu—NH₂

Condensation of Z—Pro—OH (47.12 g.) and HOSu (22.78 g.) using dicyclohexylcarbodiimide (39.04 g.) in dimethylformamide (400 ml.) at ice-ethanol temperature for four hours and recrystallization of the product from ethyl acetate gave Z—Pro—OSu (39.8 g., 61% yield).

Condensation of Z—Pro—OSu (39.8 g.) and the potassium salt of H—trp—OH (formed from 30.36 g. of HtrpOH and 6.45 g. of potassium hydroxide) in water (100 ml.)-dimethylformamide (350 ml.) at ice-salt temperature during mixing of the reactants and then at room temperature overnight and isolation of the product by stripping it from cyclohexane-ethyl acetate gave Z—Pro—trp—OH as a foam.

Condensation of Z—Phe—OH (44.85 g.) and H—trp—OCH₃ hydrochloride salt (38.25 g.) by the mixed anhydride method using isobutyl chloroformate (20.85 g.) and N-methylmorpholine (two 15.15 g. portions) in tetrahydrofuran (700 ml.) and dimethylformamide (250 ml.) at −20° C. to −15° C. for two hours and then at room temperature for two hours and isolation of the product by ethyl acetate extraction gave Z—Phe—trp—OCH₃ as a white solid (78.6 g., theory 74.85 g.).

Debenzyloxycarbonylation of Z—Phe—trp—OCH₃ (20.0 g.) by hydrogenation in a Parr shaker with palladium-on-carbon (10%, 2.0 g.) in glacial acetic acid (230 ml.) for two hours 50 minutes at room temperature and crystallization of the crude product from ethyl acetate-hexane-methanol gave H—Phe—trp—OCH₃ acetate salt as a white solid 15.200 g., 89.2% yield).

Condensation of Z—Pro—trp—OH (35.24 g.) and H—Phe—trp—OCH₃ acetate salt (34.08 g.) using dicyclohexylcarbodiimide (16.48 g.), N-hydroxysuccinimide (9.20 g.) and N-methylmorpholine (8.09 g.) in tetrahydrofuran (600 ml.) at −10° C. during mixing of the reactants and then at room temperature overnight, isolation of the crude product by ethyl acetate extraction, and purification thereof by high pressure liquid chromatography on silica gel using ethyl acetate-hexane (4:1) as eluant gave Z—Pro—trp—Phe—trp—OCH₃ (26.0 g., 42% yield).

Condensation of Z—Pro—trp—Phe—trp—OCH₃ (23.0 g.) and hydrazine hydrate (15 ml.) in ethanol (250 ml.) at room temperature overnight gave Z—Pro—trp—Phe—trp—NHNH₂ (19.1 g., 83% yield).

Condensation of Z—Pro—trp—Phe—trp—NHNH₂ (1.14 g.) and H—Leu—NH₂ hydrobromide salt (306 mg.) by the acyl azide method using butyl nitrite (187 μl.), hydrogen chloride (2.55N in dimethylformamide, 0.63 ml.) and diisopropylethylamine (582 mg.) at 0° C. during mixing of the reactants and in the refrigerator over the weekend, isolation of the crude product by ethyl acetate extraction, and purification thereof by high pressure liquid chromatography on silica gel using ethyl acetate-isopropyl alcohol (99:1) as eluant gave Z—Pro—trp—Phe—trp—Leu—NH₂ (912 mg., 71% yield).

Debenzyloxycarbonylation of Z—Pro—trp—Phe—trp—Leu—NH₂ (665 mg.) by hydrogenation in a Parr shaker with palladium-on-carbon (10%, 350 mg.) in glacial acetic acid (50 ml.), purification of the crude product by high pressure liquid chromatography on octadecylsilated silica gel using methanol-water (70:30) containing ammonium acetate (0.2%) as eluant, and lyophilization of the purified product from acetic acid gave H—Pro—trp—Phe—trp—Leu—NH₂ as the amorphous white solid triacetate hydrate salt-solvate (340 mg., 36% yield).

EXAMPLE 4

H—tpi—Phe—trp—Leu—Met—NH₂

H—tpi—OH was prepared by the method of Lippke et al. (J. Med. Chem., vol. 26, pp. 500-503, 1983) from D-tryptophan sodium salt (prepared from 20 g. of D-tryptophan and 3.9 g. of sodium hydroxide) and aqueous formaldehyde (37%, 15.9 g.) in water (50 ml.). The product was obtained by crystallization in two crops (12.77 g., m.r. 290°-292° C.; 4.31 g., m.r. 292°-295° C.; 81% yield).

Boc—tpi—OH was prepared from H—tpi—OH (2.9 g.) and di-t-butyl dicarbonate (3.7 g.) in dioxane (30 ml.)-water (30 ml.) containing triethylamine (2.8 ml.) at room temperature. The crude product was crystallized from methanol in three crops (0.36 g., m.p. 320° C. with decomposition; 1.05 g.; 0.69 g.; 84% yield).

Boc—Phe—trp—OH was prepared from Boc—Phe—OSu (7.24 g.) and H—trp—OH (4.10 g.) using tetramethylguanidine (2.3 g.) in dimethylformamide (200 ml.) at ice temperature for one hour and than at room temperature overnight. The crude product was recrystallized from ethyl acetate-hexane in three crops (7.35 g., 0.615 g., 0.730 g.; 96.4% yield).

Boc—Phe—trp—Leu—Met—NH$_2$ was prepared by condensation of Boc—Phe—trp—OH (4.51 g.) and H—Leu—Met—NH$_2$ hydrochloride salt (example 1 of above-cited U.S. Pat. No. 4,472,305, 2.795 g.) using dicyclohexylcarbodiimide (2.06 g.), 1-hydroxybenzotriazole hydrate (1.56 g.) and N-methylmorpholine (1.01 g.) in dichloromethane (60 ml.)-dimethylformanide (20 ml.) at ice temperature for two hours and then at room temperature overnight. The crude product (7.57 g.) was purified by reverse phase high pressure liquid chromatography on octadecylsilated silica gel using methanol-water (78:22) as eluant and was isolated as the amorphous white solid hemihydrate (5.27 g., 76% yield).

De-t-butyloxycarbonylation of BocPhe—trp—Leu—MetNH$_2$ (4.1 g.) using trifluoroacetic acid-water (70:30, 85 ml.) at room temperature gave H—Phe—trp—Leu—Met—NH$_2$ trifluoroacetate salt as a pinkish foam (4.27 g.; theory, 4.17 g.).

Condensation of Boc—tpi—OH (316 mg.) and H—Phe—trp—Leu—Met—NH$_2$ trifluoroacetate salt (708 mg.) using dicyclohexylcarbodiimide (206 mg.), 1-hydroxybenzotriazole hydrate (153 mg.) and diisopropylethylamine (129 mg.) in dichloromethane-dimethylformamide (1:1, 30 ml.) at ice temperature for three hours and then at room temperature overnight and crystallization of the crude product from ethyl acetate-hexane gave Boc—tpi—Phe—trp—Leu—Met—NH$_2$ as a white solid in two crops (710 mg., m.r. 146°-147° C.; 120 mg.; 93.1% yield).

De-t-butyloxycarbonylation of Boc—tpi—Phe—trp—Leu—Met—NH$_2$ (600 mg.) using trifluoroacetic acid-water (60:40, 60 ml.) at room temperature, purification of the crude product (640 mg.) by reverse phase high pressure liquid chromatography on octadecylsilated silica gel using methanol-water (60:40) containing trifluoroacetic acid (0.2%) as eluant, and conversion of the product into the phosphate salt by ion exchange chromatography followed by lyophilization from glacial acetic acid gave H—tpi—Phe—trp—Leu—Met—NH$_2$ as the amorphous white solid phosphate salt (1:1) hydrate (2:7) (188 mg., 29% yield).

EXAMPLE 5

H—Tpi—Phe—trp—Leu—Met—NH$_2$

Boc—Tpi—OH was prepared from H—Tpi—OH (above-cited Lippke et al., J. Med. Chem., vol. 26, pp. 500-503, 1983; 4.32 g.) and di-t-butyl dicarbonate (4.75 g.) in dioxane (60 ml.)-water (50 ml.) at room temperature while maintaining the pH at 9 with sodium hydroxide (1N). The product was isolated by ether extraction of an acidified aqueous solution and purified by trituration and crystallization from ether in two crops (1.965 g., 1.71 g.; 58% yield).

Condensation of Boc—Tpi—OH (632 mg.) and H—Phe—trp—Leu—Met—NH$_2$ trifluoroacetate salt (example 4, 1.416 g.) using dicyclohexylcarbodiimide (412 mg.), 1-hydroxybenzotriazole hydrate (306 mg.) and diisopropylethylamine (258 mg.) in dichloromethane-dimethylformamide (1:1, 50 ml.) at ice temperature for one and one half hours and then at room temperature overnight and crystallization of the crude product from ethyl acetate-hexane gave Boc—Tpi—Phe—trp—Leu—Met—NH$_2$ as an off-white solid (1.026 g., 57.5% yield).

De-t-butyloxycarbonylation of Boc—Tpi—Phe—trp—Leu—Met—NH$_2$ (940 mg.) using trifluoroacetic acid-water (70:30, 100 ml.) at room temperature for one and one half hours, purification of the crude product (1.225 g.) by reverse phase high pressure liquid chromatography on octadecylsilated silica gel in two passes using methanol-water (75:25) containing trifluoroacetic acid (0.2%) as eluant in the first pass and methanol-water (70:30) containing trifluoroacetic acid (0.2%) as eluant in the second pass, and conversion of the product into the phosphate salt by ion exchange chromatography followed by lyophilization from glacial acetic acid gave H—Tpi—Phe—trp—Leu—Met—NH$_2$ as the amorphous pale yellow solid phosphate salt (1:1) acetic acid solvate (4:7) 392 mg., 37.4% yield).

EXAMPLE 6

H—Pro—trp—Phe—tpi—Leu—Phe—NH$_2$

Condensation of Boc—Leu—OH monohydrate (12.45 g.) and H—Phe—NH$_2$ hydrochloride salt (10.025 g.) by the mixed anhydride method using isobutyl chloroformate (6.95 g.) and N-methylmorpholine (two 5.05 g. portions) in tetrahydrofuran (500 ml.) and dimethylformamide (150 ml.) first at −25° C. for two hours and then at room temperature overnight gave Boc—Leu—Phe—NH$_2$ as a white foam (18.375 g., 97.5% yield).

De-t-butyloxycarbonylation of Boc—Leu—Phe—NH$_2$ (17.60 g.) using hydrogen chloride in ethyl acetate (4.4N, 150 ml.) for one and one half hours at room temperature and trituration of the crude product with ether gave H—Leu—Phe—NH$_2$ hydrochloride salt as a white solid (14.145 g., 96.7% yield).

Condensation of Boc—trp—OH (13.07 g.) and H—Leu—Phe—NH$_2$ hydrochloride salt (13.48 g.) by the mixed anhydride method using isobutyl chloroformate (6.00 g.) and N-methylmorpholine (two 4.343 g. portions) in tetrahydrofuran (400 ml.) and dimethylformamide (150 ml.) first at −25° C. for two hours and then at room temperature overnight gave Boc—trp—Leu—Phe—NH$_2$ as a light pink foam (24.2 g., 100% yield).

De-t-butyloxycarbonylation of Boc—trp—Leu—Phe—NH$_2$ (22 g.) using trifluoroacetic acid-water (70:30, 500 ml.) for one and one half hours at room temperature and isolation of the product by ethyl acetate extraction gave H—trp—Leu—Phe—NH$_2$ as an off-white solid (15.32 g., 84.7% yield).

Condensation of H—trp—Leu—Phe—NH$_2$ (4.63 g.) and aqueous formaldehyde (37%, 0.83 g.) in glacial acetic acid (60 ml.) for two hours at room temperature and isolation of the product by a combination of ethyl acetate extraction and filtration gave H—tpi—Leu—Phe—NH$_2$ as a white solid (2.77 g., 58.3% yield).

Condensation of a solution of (Boc—Phe)$_2$O (prepared from 7.95 g. of Boc—Phe—OH and 3.09 g. of dicyclohexylcarbodiimide at −10° C. for one hour) in dichloromethanedimethylformamide (80:20, 80 ml.) and a solution of Htpi—Leu—PheNH$_2$ (3.485 g.) in dimethylformamide (50 ml.) at ice temperature for four hours and at room temperature for one half hour followed by storage in the refrigerator over the weekend and purification of the crude ethyl acetate extraction product (6.70 g.) by high pressure liquid chromatography on silica gel using methanol-water (80:20) as eluant gave Boc—Phe—tpi—Leu—Phe—NH₂ as a white solid (3.678 g., 69.4% yield).

De-t-butyloxycarbonylation of Boc—Phe—tpi—Leu—Phe—NH₂ using hydrogen chloride in ethyl acetate (4.4N, 120 ml.) for 40 minutes at room temperature and purification of the resulting light yellowish solid (2.44 g.) by high pressure liquid chromatography on silica gel using methanol-water (70:30) as eluant gave H—Phe—tpi—Leu—Phe—NH₂ hydrochloride salt, part (0.900 g.) as the hemihydrate and part (1.100 g.) as the sesquihydrate (95% yield).

Boc—Pro—trp—OH (part B of example 17 of above-cited U.S. Pat. No. 4,472,305, 1.00 g.) and H—Phe—tpi—Leu—Phe—NH₂ (formed from 690 mg. of the hydrochloride salt hemihydrate and 830 mg. of the hydrochloride salt sesquihydrate by evaporation under vacuum from a solution in 50 ml. of dimethylformamide containing 250 mg. of triethylamine and further evaporation from dichloromethane, 2.48 millimole) were condensed using dicyclohexylcarbodiimide (515 mg.) and 1-hydroxybenzotriazole hydrate (380 mg.) in dimethylformamide (45 ml.) at ice temperature for three hours and then at room temperature overnight. The crude product (2.26 g.) was isolated by dichloromethane extraction and purified by reverse phase high pressure liquid chromatography on octadecylsilated silica gel using methanol-water (80:20) as eluant, affording Boc—Pro—trp—Phe—tpi—Leu—Phe—NH₂ as a yellowish solid (553 mg., 23% yield).

De-t-butyloxycarbonylation of Boc—Pro—trp—Phe—tpi—Leu—Phe—NH₂ (507 mg.) using trifluoroacetic acid-water (70:30, 50 ml.) at room temperature for 40 minutes and conversion of the product into the phosphate salt by ion exchange chromatography followed by lyophilization from glacial acetic acid gave H—Pro—trp—Phe—tpi—Leu—Phe—NH₂ as the amorphous light yellow solid phosphate salt (1:1) acetic acid solvate (1:2) (455 mg., 80% yield).

EXAMPLE 7

H—Tpi—Bpa—trp—Leu—Phe—NH₂
H—Tpi—bpa—trp—Leu—Phe—NH₂ (mixture of isomers)

In this example Bpa represents L-β-(2-pyridyl)-alanyl and bpa represents D-β-(2-pyridyl)alanyl.

Condensation of a racemic mixture of Boc—Bpa—OH and Boc—bpa—OH (Agafonova et al., Zh. Obshch. Khim., vol. 40, no. 11, 1970, pp. 2502-2507; Chemical Abstracts, vol. 75, 1971, abst. 118574s; 2.29 g.) and H—trp—Leu—Phe—NH₂ (example 6, 4.00 g.) using dicyclohexylcarbodiimide (1.80 g.) and 1-hydroxybenzotriazole hydrate (1.16 g.) in tetrahydrofuran (200 ml.) for two hours at 0° C. and then overnight at room temperature and isolation of the product by ethyl acetate extraction gave Boc—Bpa—trp—Leu—Phe—NH₂ and Boc—bpa—trp—Leu—Phe—NH₂ as a mixture of isomers.

De-t-butyloxycarbonylation of the isomeric mixture of Boc—Bpa—trp—Leu—Phe—NH₂ and Boc—bpa—trp—Leu—Phe—NH₂ (4.6 g.) using trifluoroacetic-water (70:30, 250 ml.) at room temperature for one half hour gave H—Bpa—trp—Leu—Phe—NH₂ and H—bpa—trp—Leu—Phe—NH₂ as a mixture of isomers.

Condensation of Boc—Tpi—OH (example 5, 1.3 g.) and the isomeric mixture of H—Bpa—trp—Leu—Phe—NH₂ and H—bpa—trp—Leu—Phe—NH₂ (2.00 g.) using dicyclohexylcarbodiimide (0.67 g.) and 1-hydroxybenzotriazole hydrate (0.50 g.) in dichloromethane-dimethylformamide (1:1, 60 ml.) for two hours at 0° C. and then overnight at room temperature and isolation of the product by ethyl acetate extraction gave Boc—Tpi—Bpa—trp—Leu—Phe—NH₂ and Boc—Tpi—bpa—trp—Leu—Phe—NH₂ as a mixture of isomers.

De-t-butyloxycarbonylation of the isomeric mixture of Boc—Tpi—Bpa—trp—Leu—Phe—NH₂ and Boc—Tpi—bpa—trp—Leu—Phe—NH₂ (675 mg.) using trifluoroacetic acid-water (4:1, 40 ml.) at room temperature for one hour and isolation and purification of the crude product by ethyl acetate extraction, column chromatography on silica gel (75 g.) using ethyl acetate-pyridine-acetic acid-water (400:56:14:30) as eluant, lyophilization (370 mg., 62% yield), conversion into the hydrochloride salt, lyophilization (385 mg.), reverse phase high pressure liquid chromatography on octadecylsilated silica gel using methanol-water (65:35) containing ammonium acetate (0.2%) as eluant and two lyophilizations gave an isomeric mixture of H—Tpi—Bpa—trp—Leu—Phe—NH₂ and H—Tpi—bpa—trp—Leu—Phe—NH₂ as the amorphous white solid trihydrochloride salt dihydrate (234 mg., 33% yield).

EXAMPLE 8

H—trp—Phe—trp—Leu—Phe—NH₂

Condensation of Boc—trp—Phe—OH (example 1, 7.67 g.) and H—trp—Leu—Phe—NH₂ (example 6, 7.875 g.) using dicyclohexylcarbodiimide (3.51 g.) and N-hydroxysuccinimide (1.96 g.) in tetrahydrofuran (250 ml.) for one hour at −10° C. and then over the weekend at room temperature, isolation of the crude product by ethyl acetate extraction and crystallization thereof from ethyl acetate-hexane gave Boc—trp—Phe—trp—Leu—Phe—NH₂ (10.45 g., m.r. 170°-173° C., 71% yield.)

De-t-butyloxycarbonylation of Boc—trp—Phe—trp—Leu—Phe—NH₂ (6.57 g.) using trifluoroacetic acid-water (80:20, 100 ml.) for one half hour at room temperature, isolation of the crude product by ethyl acetate extraction, purification thereof by reverse phase high pressure liquid chromatography on octadecylsilated silica gel using methanol-water (75:25) containing ammonium acetate (0.2%) as eluant followed by lyophilization from glacial acetic acid, and conversion of half of the product (2.65 g.) into the phosphate salt by ion exchange chromatography using methanol-water (1:1) as eluant followed by lyophilization gave H—trp—Phe—trp—Leu—Phe—NH₂ as the white solid phosphate salt (1.32 g., m.r. 218°-221° C. with decomposition, 38% yield).

EXAMPLE 9

H—tpi—Phe—trp—Leu—Phe—NH₂

Condensation of H—trp—Phe—trp—Leu—Phe—NH₂ (example 8, 2.12 g.) and aqueous formaldehyde (37%, 0.24 g.) in glacial acetic acid for three hours at room temperature, crystallization of the crude product from ethyl acetate, and conversion of the product (1.44 g.) into the phosphate salt by ion exchange chromatography using methanol-water (4:1) as eluant followed by lyophilization gave H—tpi—Phe—trp—Leu—Phe—NH₂ as the amorphous yellow solid phosphate salt (1:1) hemihydrate methanol solvate (2:1) (969 mg., 39% yield).

BIOLOGICAL PROPERTIES OF THE COMPOUNDS

As stated above the peptide amides of the three composition of matter aspects of the invention are useful as Substance P agonists and/or antagonists and are therefore useful as antihypertensives and/or analgesics. These utilities are shown by a test for tritiated Substance P ($^3$H-SP) competitive binding in rat brain tissue, a test for Substance P agonist and antagonist effect in the isolated guinea pig ileum, and a test for protection against acetylcholine-induced writhing in the mouse.

RAT BRAIN TISSUE $^3$H-SP COMPETITIVE BINDING

Crude rat brain tissue is suspended in buffer containing protease inhibitors and calcium ions and magnesium ions and incubated under nitrogen atmosphere with $^3$H-SP and test compound. The bound SP is then separated from free SP by filtration and quantitated by liquid scintillation spectroscopy. This test meets the criteria of reversibility, saturability, sensitivity to known SP agonists and antagonists, and specificity for an SP receptor binding assay.

With regard to reversibility, addition of unlabelled SP causes a gradual decrease in bound $^3$H-SP, showing that SP is not irreversibly bound to the receptors in the tissue. With regard to saturability, the amount of bound $^3$H-SP in the preparation increases in direct proportion to the concentration of $^3$H-SP added until a saturation point is reached. A Scatchard analysis of these data suggests that a single receptor is involved and that $^3$H-SP has a high affinity for this receptor. With regard to sensitivity, known SP agonists and antagonists inhibit $^3$H-SP binding. With regard to specificity, known substances structurally unrelated to SP including capsaicin and baclofen do not affect $^3$H-SP binding.

The results are expressed in terms of the equilibrium constant $K_D$ in nanomoles per liter (nM), which takes into account the concentration of $^3$H-SP. The following results were obtained.

| Peptide Amide of Example | Substance P Competitive Binding $K_D$ (nM) |
| --- | --- |
| 2 | 22 |
| 3 | 35 |
| 4 | 42 |
| 5 | 59 |
| 6 | 39 |

GUINEA PIG ILEUM TEST

Strips of longitudinal muscle (derived from terminal ileum of adult male guinea pigs (Charles River, 400-600 g.) are mounted in 5-ml. organ baths containing oxygenated Krebs solution containing 1 $\mu$M each of atropine and pyrilamine maintained at 30°-33° C. and connected to isometric transducers. Following tissue equilibration and repeated washing (45-60 min.), SP or an appropriate reference agonist is added cumulatively to the bath and contractions of the tissue are recorded. The bath is washed thoroughly and 30-45 min. is allowed to elapse before construction of a second reference agonist curve to assure reproducibility of the responses. Test compounds are similarly evaluated for agonist activity up to a maximum concentration of 10-100 $\mu$M. Regression analysis of the linear portion of the log concentration-percent maximal response curves provides the EC50 (and 95% confidence limits), the standard measure of agonist potency. When appropriate, relative molar potency ratios are calculated (EC50 reference/ED50 test drug). Antagonist activity is examined by pretreating thoroughly washed tissues with test compound (using a standard 5-10 min. contact time), then constructing a cumulative dose-response curve to the reference agonist. The effects of several concentrations of test antagonist, pooled across separate experiments, provide dose-ratio (EC50 shift) data for a standard Schild plot analysis, with computation of the $pA_2$.

The following results were obtained.

| Peptide Amide of Example | Substance P Antagonist $pA_2$ |
| --- | --- |
| 2 | 6.4 |
| 3 | 5.1 |
| 4 | 6.4 |
| 6 | 6.4 |
| 7 | 6.25 |
| 8 | 6.28 |
| 9 | 6.65 |

The peptide amide of example 1 showed evidence of utility as a Substance P agonist in this test. Some agonist activity was noted but it was not quantified. The EC50 value was shown to be $>1$ $\mu$M.

MOUSE ACETYLCHOLINE-INDUCED WRITHING TEST

Male Swiss-Webster mice (18-24 g.) are divided into groups of 8-15 mice. A test compound in a vehicle or the vehicle alone is administered intrathecally in a volume of 5 $\mu$l by the method of Hylden and Wilcox (European Journal of Pharmacology, vol. 67, pp. 313-316, 1980) except that caudal cutaneous incision is not performed prior to injection. Five minutes after the injection a solution of acetylcholine (3.2 mg./kg., the approximate ED90) in 0.9% aqueous sodium chloride is administered intraperitoneally to each mouse. A mouse not exhibiting one or more writhes during the next two-minute observation period is considered protected by the test compound. For test compounds which produce a graded dose-response ED50 values with 95% confidence limits are determined by probit analysis of the data.

In this test an ED50 value of 0.7 $\mu$g/mouse was obtained for the peptide amide of example 4.

The peptide amides of the three composition of matter aspects of the invention can be prepared for use as Substance P agonists and/or antagonists and as antihypertensives and/or analgesics for oral or parenteral administration in liquid or solid dosage form as solutions, suspensions, emulsions, capsules or tablets with conventional pharmaceutical vehicles and adjuncts by conventional pharmaceutical techniques.

We claim:
1. The peptide amide having the structural formula

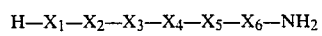

wherein
X$_1$ is a direct linkage or Pro;
X$_2$ is trp, Tpi, or tpi;
X$_3$ is Phe, Bpa or bpa;
X$_4$ is trp or tpi;
X$_5$ is Leu or a direct linkage; and $X_6$ is Phe or a direct linkage; or a pharmaceutically acceptable acid addition salt or solvate or acid addition salt-solvate thereof.

2. The peptide amide having the structural formula $$H-X_1-X_2-X_3-X_4-X_5-X_6-NH_2$$

wherein
$X_1$ is a direct linkage or Pro;
$X_2$ is trp, Tpi, or tpi;
$X_3$ is Phe, Bpa or bpa;
$X_4$ is trp or tpi;
$X_5$ is Leu or a direct linkage; and
$X_6$ is Met, Phe or a direct linkage;
except that at least one of $X_2$ and $X_4$ is other than trp; or a pharmaceutically acceptable acid addition salt or solvate or acid addition salt-solvate thereof.

3. The peptide amide according to claim 2 wherein $X_1$ is a direct linkage, $X_2$ is Tpi or tpi, $X_3$ is Phe, $X_4$ is trp, $X_5$ is Leu and $X_6$ is Met or a pharmaceutically acceptable acid addition salt or solvate or acid addition salt-solvate thereof.

4. H—tpi—Phe—trp—Leu—Met—NH$_2$ phosphate salt (1:1) hydrate (2:7) according to claim 3.

5. H—Tpi—Phe—trp—Leu—Met—NH$_2$ phosphate salt (1:1) acetic acid solvate (4:7) according to claim 3.

6. The peptide amide according to claim 2 wherein $X_1$ is Pro, $X_2$ is trp, $X_3$ is Phe, $X_4$ is tpi, $X_5$ is Leu and $X_6$ is Phe or a pharmaceutically acceptable acid addition salt or solvate or acid addition salt-solvate thereof.

7. H—Pro—trp—Phe—tpi—Leu—Phe—NH$_2$ phosphate salt (1:1) acetic acid solvate (1:2) according to claim 6.

8. The peptide amide according to claim 2 wherein $X_1$ is a direct linkage, $X_2$ is Tpi, $X_3$ is Bpa or bpa, $X_4$ is trp, $X_5$ is Leu and $X_6$ is Phe or a pharmaceutically acceptable acid addition salt or solvate or acid addition salt-solvate thereof.

9. An isomeric mixture of H—Tpi—Bpa—trp—Leu—Phe—NH$_2$ and H—Tpi—bpa—trp—Leu—Phe—NH$_2$ trihydrochloride salt dihydrate according to claim 8.

10. The peptide amide according to claim 2 wherein $X_1$ is a direct linkage, $X_2$ is tpi, $X_3$ is Phe, $X_4$ is trp, $X_5$ is Leu and $X_6$ is Phe or a pharmaceutically acceptable acid addition salt or solvate or acid addition salt-solvate thereof.

11. H—tpi—Phe—trp—Leu—Phe—NH$_2$ phosphate salt (1:1) methanol solvate (2:1) according to claim 10.

12. The peptide amide having the structural formula $$H-X_1-X_2-X_3-X_4-X_5-X_6-NH_2$$

wherein
$X_1$ is a direct linkage or Pro;
$X_2$ is trp, Tpi, or tpi;
$X_3$ is Phe, Bpa or bpa;
$X_4$ is trp or tpi;
$X_5$ is Leu or a direct linkage; and
$X_6$ is Phe or a direct linkage;
except that when $X_2$ is trp $X_4$ is also trp; or a pharmaceutically acceptable acid addition salt or solvate or acid addition salt-solvate thereof.

13. The peptide amide according to claim 12 wherein $X_1$ is a direct linkage, $X_2$ is trp, $X_3$ is Phe, $X_4$ is trp, $X_5$ is Leu and $X_6$ is Phe or a pharmaceutically acceptable acid addition salt or solvate or acid addition salt-solvate thereof.

14. H—trp—Phe—trp—Leu—Phe—NH$_2$ phosphate salt (1:1) hemihydrate methanol solvate (2:1) according to claim 13.

15. The peptide amide according to claim 12 wherein $X_1$ is Pro, $X_2$ is trp, $X_3$ is Phe, $X_4$ is trp, $X_5$ is Leu and $X_6$ is Phe or a pharmaceutically acceptable acid addition salt or solvate or acid addition salt-solvate thereof.

16. H—Pro—trp—Phe—trp—Leu—Phe—NH$_2$ phosphate salt (1:1) according to claim 15.

17. The peptide amide according to claim 12 wherein $X_1$ is Pro, $X_2$ is trp, $X_3$ is Phe, $X_4$ is trp, $X_5$ is Leu and $X_6$ is a direct linkage or a pharmaceutically acceptable acid addition salt or solvate or acid addition salt-solvate thereof.

18. H—Pro—trp—Phe—trp—Leu—NH$_2$ triacetate hydrate salt-solvate according to claim 17.

* * * * *